United States Patent
Chang et al.

(10) Patent No.: US 7,772,337 B2
(45) Date of Patent: Aug. 10, 2010

(54) METHOD OF FORMULATING A MOLECULAR SIEVE CATALYST COMPOSITION BY CONTROLLING COMPONENT ADDITION

(75) Inventors: Yun-feng Chang, Houston, TX (US); Stephen N. Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 374 days.

(21) Appl. No.: 11/859,227

(22) Filed: Sep. 21, 2007

(65) Prior Publication Data

US 2009/0082545 A1   Mar. 26, 2009

(51) Int. Cl.
C08F 4/00 (2006.01)
(52) U.S. Cl. ............................................. 526/90
(58) Field of Classification Search .................. 526/90
See application file for complete search history.

(56) References Cited

U.S. PATENT DOCUMENTS

| | | | |
|---|---|---|---|
| 5,783,726 A | 7/1998 | Lemanski et al. | |
| 5,833,840 A | 11/1998 | Absil et al. | |
| 6,153,552 A | 11/2000 | Wachter et al. | |
| 6,455,628 B1 | 9/2002 | Ma et al. | |
| 6,528,447 B1 | 3/2003 | Ghosh et al. | |
| 6,710,003 B2 | 3/2004 | Jan et al. | |
| 6,872,680 B2 | 3/2005 | Chang et al. | |
| 7,037,876 B2 | 5/2006 | O'Brien et al. | |
| 2004/0121902 A1 | 6/2004 | Chang et al. | |
| 2004/0266615 A1 | 12/2004 | Watson et al. | |
| 2007/0100187 A1 | 5/2007 | Chang | |

FOREIGN PATENT DOCUMENTS

| WO | WO 99/21651 | 5/1999 |
|---|---|---|
| WO | 03/000413 | 1/2003 |
| WO | 2005/107944 | 11/2005 |

*Primary Examiner*—Ling-Siu Choi
*Assistant Examiner*—Sonya Wright
(74) *Attorney, Agent, or Firm*—Kevin M. Faulkner; David M. Weisberg

(57) ABSTRACT

This invention provides a method of making a molecular sieve catalyst composition comprising the steps of: a) combining molecular sieve crystals with binder and liquid to form a binder-sieve mixture; b) combining the binder-sieve mixture with matrix material to form a binder-sieve-matrix mixture; c) mixing the binder-sieve-matrix mixture under conditions sufficient to form a slurry having a solids content of at least 40 wt %, based on total weight of the slurry; d) progressing the mixing until slurry viscosity decreases without significant additional dilution of the slurry, so that the slurry solids content does not significantly decrease; and e) drying the decreased viscosity slurry to produce a dried molecular sieve catalyst composition having an attrition rate index of not greater than 1 wt %/hr. The aforementioned catalyst compositions can be used in processes for making olefin product from oxygenate feedstock, which olefin products can be further used for making (co)polymer products.

20 Claims, 1 Drawing Sheet

METHOD OF FORMULATING A MOLECULAR SIEVE CATALYST COMPOSITION BY CONTROLLING COMPONENT ADDITION

FIELD OF THE INVENTION

This invention relates to methods of making and using molecular sieve catalyst. In particular, the invention relates to methods of making molecular sieve catalysts that reduce or minimize the energy needed to thoroughly mix the components.

BACKGROUND OF THE INVENTION

A desirable characteristic for certain molecular sieve catalysts, regardless of the process of use, is that the finished or formulated catalyst be attrition resistant. Attrition resistance can refer to hardness as well as ability to absorb shock, since the catalyst will typically have to endure severe stress in commercial scale processes.

For example, WO 99/21651 describes a method for making molecular sieve catalyst that is considered relatively hard. The method includes the steps of mixing together a molecular sieve and an alumina sol, the alumina sol being made in solution and maintained at a pH of 2 to 10. The mixture is then spray dried and calcined. The calcined product is reported to be relatively hard.

U.S. Pat. No. 6,153,552 describes another method for making molecular sieve catalyst. The catalyst is made by mixing together a silicon-containing oxide sol as a binder material and a molecular sieve material. The pH of the mixture is adjusted prior to spray drying. Following spray drying, the catalyst material is calcined to form a finished catalyst product, which is reported to be relatively hard.

U.S. Pat. No. 6,455,628 describes a process for preparing an aqueous dispersion by wet milling an aqueous carrier medium, a particulate solid, and a polymeric dispersant that is composed of at least 50 wt % of a block copolymer.

U.S. Pat. No. 6,872,680 describes methods for making molecular sieve catalyst compositions having improved attrition resistance by forming a slurry by combining a molecular sieve, a binder, and a matrix material, wherein the slurry has a pH above or below the isoelectric point (IEP) of the molecular sieve.

U.S. Patent Application Publication No. 2007/0100187 describes processes for making attrition resistant molecular sieve catalyst compositions by initially mixing together catalyst components to form a slurry at a relatively low viscosity and high solids content using a rotor-stator mixer.

Attrition resistance continues to be a desirable characteristic in molecular sieve catalysts. As new process systems are developed, the ability of the catalyst to endure the stress of the process system is particularly important so as to increase the effective life of the catalyst in the reaction process. If the catalyst is not properly attrition resistant, it is likely to break apart at an early stage, meaning that the catalyst could only be effectively used for a relatively short period of time. Therefore, obtaining molecular sieve catalysts that have a high degree of attrition resistance are still sought. Methods that are particularly effective at making highly attrition resistant molecular sieve catalysts at commercial scale are in particularly high demand.

In addition, reducing or minimizing the energy used in mixing can be particularly advantageous, and may even be necessary, in methods for fabricating molecular sieve catalysts that have a high degree of attrition resistance.

SUMMARY OF THE INVENTION

One aspect of the invention relates to a method of making a molecular sieve catalyst composition comprising the steps of:

a) combining molecular sieve crystals with binder and liquid to form a binder-sieve mixture;

b) combining the binder-sieve mixture with matrix material to form a binder-sieve-matrix mixture;

c) mixing the binder-sieve-matrix mixture under conditions sufficient to form a slurry having a solids content of at least 40 wt %, based on total weight of the slurry;

d) progressing the mixing until slurry viscosity decreases without significant additional dilution of the slurry, so that the slurry solids content does not significantly decrease; and e) drying the decreased viscosity slurry to produce a dried molecular sieve catalyst composition having an attrition rate index of not greater than 2.0 wt %/hr, wherein the combining in step b) and the mixing in step c) result in a maximum viscosity below 30,000 cPs, wherein the decreased viscosity slurry formed in step d) has a final viscosity not greater than 15,000 cPs, and wherein the ratio of the final viscosity to the maximum viscosity is from 20% to 65%.

Another aspect of the invention relates to a process for making an olefin product from an oxygenate feedstock comprising the steps of:

a) making a dried molecular sieve catalyst composition according to the method of the instant invention; and b) contacting the dried metalloaluminophosphate molecular sieve catalyst with the oxygenate feedstock under conditions sufficient to form the olefin product comprising ethylene and propylene, wherein the selectivity of the dried metalloalumino-phosphate molecular sieve catalyst for the combination of ethylene and propylene is at least 70%.

Another aspect of the invention relates to a process for making a (co)polymer product comprising the steps of:

a) making an olefin product comprising ethylene and propylene from an oxygenate feedstock according to the method of the instant invention; and b) contacting at least one of the ethylene and propylene from the olefin product, and optionally one or more other polymerizable monomers, with a polymerization catalyst under conditions sufficient to form the (co)polymer product, wherein the (co)polymer product comprises a combined ratio of ethylene and/or propylene repeat units to other polymerizable monomer repeat units that is more than 50 wt %.

These aspects of the invention can advantageously result in reduced or minimized mixing energy used, which can translate in more economical processes and products. These more economical processes and products are further described in more detail below.

DETAILED DESCRIPTION OF THE INVENTION

Figure 1:
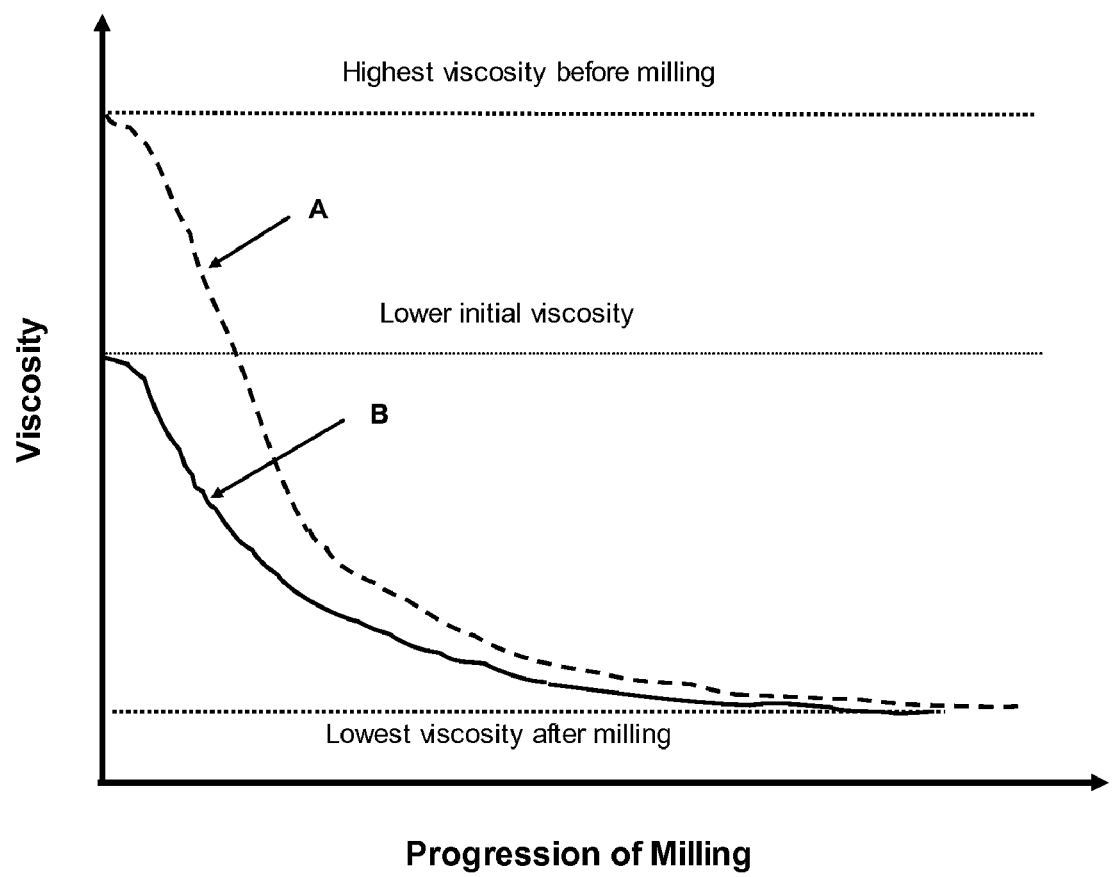
FIG. 1 is an illustration of viscosity behavior of slurries as a function of milling, wherein: (A) the slurry is made by combining together a molecular sieve, a binder, and a matrix material; and (B) the slurry is made by combining a molecular sieve and a binder, while a matrix material is added during milling.

I. Forming a High Solids, Low Viscosity Slurry

This invention provides a reduced energy process for making a molecular sieve catalyst composition. The process includes mixing together the catalyst components with liquid to form a slurry, and drying the slurry to form the catalyst.

The formation of catalyst particles can be accomplished by initially making a slurry having a relatively high solids content, while simultaneously and advantageously avoiding relatively high viscosities in that relatively high solids content slurry. In particular, the slurry can be mixed to a relatively low viscosity, taking into consideration the high solids content, and then dried, preferably by spray drying and calcining, to form the catalyst. In one embodiment, the catalyst may also have a relatively high attrition resistance.

According to this invention, attrition resistance refers to the ability to resist breaking apart, typically as a result of physical impact. Since molecular sieve catalysts are often used in fluidized-bed reaction systems or riser-type reaction systems, the ability of such catalysts to avoid physical damage within the reaction systems is important. Attrition resistance, however, does not necessarily mean that the catalyst is hard, although hardness can be a desirable characteristic. Attrition resistance can also be obtained through such characteristics as a catalyst's ability to absorb shock from impact as the catalyst is circulated through the reaction system.

II. Method of Mixing Slurry Components

This invention includes a method or step of mixing together catalyst components and liquid to form a slurry having a high solids content and a relatively low viscosity. This mixing method or step is successfully accomplished using a desired mixer having certain appropriate settings.

As is understood by those of skill in the art, selecting an efficient mixer for a particular task can be a major component to successful processing, and processing technique has come to play an increasingly vital role in maintaining competitive advantage and profit margins. Therefore, choosing the right mixer for a particular mixing process can be a somewhat complex task, and huge variations in applications have led to a particularly diverse array of mixing equipment.

In the manufacture of molecular sieve catalysts, slurries are made of molecular sieve crystals and liquid (e.g., water), and possibly numerous other ingredients depending upon the characteristics desired of the finished catalyst product. These slurries are then dried to form a final or formulated molecular sieve product. The slurry that is ultimately dried to form the final molecular sieve product can vary widely in characteristics.

According to this invention, a slurry having characteristics of high solids content and low viscosity can be achieved using a rotor-stator mixer. Rotor-stator mixers generally include a high-speed centrifugal-type rotor mounted within a stator. Typically, the stator can be held in place by frame arms.

During operation, high-speed rotor revolution can create a suction that can draw a mixture of liquid and solid materials into the center of the workhead assembly, where the mixture can be subjected to a shear force, or it can be assisted by external means (e.g., by using a feed pump). Centrifugal force can then drive the materials to the periphery of the workhead, where the mixture can encounter milling action in the clearance between the rotor blade tips and the stator inner wall. Hydraulic shear can follow, as the materials are forced out through the openings in the stator and are projected radially back into the body of the mixture.

The size and shape of openings in the stator (often referred to as the stator geometry) and the clearance between the rotor blade tips and the stator inner wall (typically referred to as gap distance) often determine the flow pattern and the machine's shear rates. For example, a stator with round holes can give a type of mixing action that is particularly suited for disintegrating solids and preparing gels, suspensions, and solutions. Slotted holes can produce a somewhat scissor-like shearing action that is particularly appropriate for disintegrating elastic or fibrous materials. Fine screens are typically used where a high degree of particle- or globule-size reduction is desired and for preparation of fine colloidal suspensions and emulsions.

Mixing, as referred to herein, can include traditional mixing methods, as well as those processes described as milling, which may occur in addition to, or instead of, the traditional mixing methods.

Mixing can be carried out using batch ("in-tank" type) mixing units or continuous ("in-line" type) mixing units, and the processes can be carried out quite effectively at commercial scale. In-tank mixers having the desired characteristics can function to form a slurry in a tank of from 1 gallon to 30,000 gallons. In-line mixers are preferred in that they can be used in a continuous manufacturing process. Such mixers are particularly suited for processing flow rates of slurry components of at least 100 liters per hour. Preferred rates of processing are at least 200 liters per hour. Mixers that can process slurry at rates of at least 400 liters per hour or at least 800 liters per hour can also be used.

Although the slurry can be mixed at relatively high viscosities, it is preferred that the maximum viscosity during mixing be as low as possible while maintaining solids content of the slurry mixture. As the mixing is progressed, the viscosity preferably decreases. In one embodiment, the slurry is mixed until the viscosity is decreased by at least about 10%, preferably by at least 15%, more preferably by at least 20%, for example by at least 30% or by at least 35% or by at least 40% or by at least 45% or by at least 50%. In some embodiments, the slurry is mixed until the ratio of the final viscosity to the initial viscosity (or to the maximum viscosity, if the maximum viscosity is higher than the initial viscosity) is from 20% to 65%, preferably from 30% to 55%, more preferably from 35% to 50%.

In any event, it is desirable that the relatively low maximum viscosity during mixing be attained without significant additional dilution of the slurry, so that the slurry solids content does not significantly decrease (e.g., decreases by no more than about 4%, preferably by no more than about 2%, more preferably by no more than about 1%, or alternately does not decrease at all).

Indeed, in a preferred embodiment, a relatively high maximum viscosity, e.g., 30,000 cPs or higher, should be avoided, such that the maximum viscosity during mixing is preferably below that value. In a particularly preferred embodiment, the maximum viscosity during mixing can advantageously be below 25,000 cPs.

The slurry product should not be too viscous as formation of highly attrition resistant catalyst particles can be adversely affected. In one embodiment, the slurry is mixed to form a slurry product having a viscosity of not greater than 15,000 cPs, preferably not greater than 14,000 cPs, for example not greater than 13,000 cPs or not greater than 12,000 cPs.

The slurry product should also be sufficiently viscous, so as to facilitate formation of catalyst particles during spray drying, which can otherwise be difficult for very low viscosity slurry products. In one embodiment, the slurry product has a viscosity of at least 500 cPs, preferably at least 1000 cPs, for example at least 1500 cPs or at least 2000 cPs.

Viscosities, such as the viscosity of the slurry, can advantageously be measured using a Brookfield DV-II+Pro Viscometer (Brookfield Instrument Laboratories Inc., Middleboro, Mass.) using a #6 spindle at about 10 rpm shear rate. The measurement is typically carried out at a temperature of about 23-24° C. The viscometer can first be calibrated with calibration standards having viscosities of 500 cPs, 1000 cPs, and 3000 cPs, before taking a measurement of the slurry samples. These calibration standards are typically certified from Brookfield Instrument Laboratories Inc., Middleboro, Mass.

The slurry can be mixed using a batch type mixing process or using an in-line mixing process. In-line mixing can be accomplished without recycle or with recycle. In a preferred embodiment, recycling is used. Preferably, the molecular sieve crystals, clay, binder and liquid are mixed with an in-line rotor-stator mixer applying recycle at a number of passes of at least 1, more preferably at least 2, and most preferably at least 3. When being milled, it is preferred that the molecular sieve crystals, clay, binder, and liquid are milled and recycled for at least 2 passes, preferably at least 5 passes, for example at least 10 passes, at least 15 passes, at least 30 passes, at least 45 passes, at least 60 passes, at least 75 passes, at least 90 passes, at least 105 passes, or at least 120 passes.

III. Slurry Components

A. Overall Composition

The catalyst of this invention is a molecular sieve catalyst composition, which comprises molecular sieve crystals, clay, and binder. Such a combination is generally referred to as a formulated catalyst. In one aspect, the formulated catalyst composition is highly attrition resistant.

B. Molecular Sieve Crystal Component

The molecular sieve particles used to make the formulated catalyst include any of a variety of molecular sieve components. The components include zeolites or non-zeolites, preferably non-zeolites. In one embodiment, the molecular sieves are small pore non-zeolite molecular sieves having an average pore size of less than about 5 angstroms, preferably an average pore size ranging from about 3 to 5 angstroms, more preferably from 3.5 to 4.5 angstroms. These pore sizes are typical of molecular sieves having 8 membered rings.

Conventional crystalline aluminosilicate zeolites having catalytic activity are desirable molecular sieves that can be used in making the catalyst of this invention. Non-limiting examples of zeolites which can be employed in the practice of this invention, include both natural and synthetic zeolites. These zeolites include zeolites of the structural types included in the *Atlas of Zeolite Framework Types*, edited by Ch. Baerlocher, W. M. Meier, D. H. Olson, Fifth Revised edition, Elsevier, Amsterdam, 2001. In one embodiment, the crystalline aluminosilicate molecular sieve can have a silica to alumina molar ratio from about 20 to about 400, for example from about 20 to about 150, from about 20 to about 100, from about 45 to about 90, from about 80 to about 350, from about 100 to about 300, from about 50 to about 200, or from about 75 to about 275.

In one preferred embodiment, the molecular sieve catalyst composition comprises an aluminosilicate catalyst composition, preferably a relatively high-silica aluminosilicate catalyst composition. Relatively high-silica aluminosilicates, as used herein, can advantageously include those having a molar relationship of $X_2O_3:(n)YO_2$ (wherein X is a trivalent element and Y is a tetravalent element), in which n is at least about 80, preferably at least about 100, for example at least about 120, at least about 150, at least about 180, or at least about 200, and typically not more than about 5000, preferably not more than about 4000, for example not more than about 3500, not more than about 3000, not more than about 2500, or not more than about 2000. Alternatively, n for relatively high-silica aluminosilicates can be from about 300 to about 4000, for example from about 300 to about 2500.

Non-limiting examples of trivalent X can include aluminum, boron, iron, indium, gallium, and combinations thereof, preferably at least including aluminum. Non-limiting examples of tetravalent Y can include silicon, tin, titanium, germanium, and combinations thereof, preferably at least containing silicon.

In embodiments where X represents aluminum and Y represents silicon, the factor n represents a silica:alumina ratio, also termed $Si:Al_2$. Another measure of relative proportion in such cases is the ratio of Y:X, or the silicon:aluminum ratio. In one embodiment, the silicon:aluminum (Si:Al) ratio of the aluminosilicates can be at least about 40, preferably at least about 50, for example at least about 60, at least about 75, at least about 90, or at least about 100, and typically not more than about 2500, preferably not more than about 2000, for example not more than about 1750, not more than about 1500, not more than about 1250, or not more than about 1000. Alternatively, the Si:Al ratio of relatively high-silica aluminosilicates can be from about 150 to about 2000, for example from about 150 to about 1250.

Other non-limiting examples of aluminosilicate catalysts and compositions can be found, for instance, in U.S. Patent Application Publication No. 2003/0176751 and U.S. patent application Ser. Nos. 11/017,286 (filed Dec. 20, 2004) and 60/731,846 (filed Oct. 31, 2005), the disclosures of each of which are incorporated by reference herein.

Additional examples of molecular sieve particles used to make formulated molecular sieve catalyst according to this invention include zeolite as well as non-zeolite molecular sieves, and are of the large, medium, or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof, the medium pore molecular sieves, AFO, AEL, EUO, HEU, FER, MEL, MFI, MTW, MTT, TON, and substituted forms thereof, and the large pore molecular sieves, EMT, FAU, and substituted forms thereof. Other molecular sieves include ANA, BEA, CFI, CLO, DON, GIS, LTL, MER, MOR, MWW, and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM, and TON. In one preferred embodiment, the molecular sieve of the invention has an AEI topology or a CHA topology, or a combination thereof, most preferably a CHA topology.

Metalloaluminophosphate molecular sieves are particularly preferred molecular sieves used in the manufacturing process of this invention. In one embodiment, these particles are represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB, and Lanthanide's of the Periodic Table of Elements, preferably M is selected from one of the group consisting of Si, Ge, Co, Cr, Cu, Fe, Ga, Ge, Mg, Mn, Ni, Sn, Ti, Zn, Zr, and mixtures thereof. In a particular embodiment, m is greater than or equal to 0.2, and x, y and z are greater than or equal to 0.01. Additionally or alternatively, in some embodiments, m can be from about 0.1 to about 1, x can be from about 0.01 to about 0.25, y can be from about 0.4 to about 0.5, and z can be from about 0.25 to about 0.5; more preferably m can be from about 0.15 to about 0.7, x can be from about 0.01 to about 0.2, y can be from about 0.4 to about 0.5, and z can be from about 0.3 to about 0.5. For the purposes of the present invention, a "templating agent" is any substance as a result of which the solid which is formed during generation of the at least one material from the synthesis mixture has at least one type of pore (micropores, mesopores, macropores).

Other examples of metalloaluminophosphate molecular sieves useful in the process of this invention include those described in EP-0 888 187 B1 (microporous crystalline metallophosphates, $SAPO_4$ (UIO-6)), U.S. Pat. No. 6,004,898 (molecular sieve and an alkaline earth metal), PCT WO 01/62382 published Aug. 30, 2001 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

Most preferably, the metalloaluminophosphate molecular sieve crystals present in the molecular sieve catalyst composition are selected from the group consisting of silicoaluminophosphate (SAPO) molecular sieves, aluminophosphate molecular sieves, and metal substituted forms thereof. Non-limiting examples of SAPO and AlPO molecular sieves that may be present in the molecular sieve catalyst of the invention include molecular sieves selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and mixtures thereof. The more preferred molecular sieves include molecular sieves selected from the group consisting of SAPO-18, SAPO-34, SAPO-35, SAPO-44, SAPO-56, AlPO-18 AlPO-34, metal containing molecular sieves thereof, and mixtures thereof; even more preferably molecular sieves selected from the group consisting of SAPO-18, SAPO-34, AlPO-34, AlPO-18, metal containing molecular sieves thereof, and mixtures thereof; and most preferably molecular sieves selected from the group consisting of SAPO-34, AlPO-18, metal containing molecular sieves thereof, and mixtures thereof.

As used herein, the term mixture is synonymous with combination and is considered a composition of matter having two or more components in varying proportions, regardless of their physical state. With regard to the molecular sieve crystal components of the catalyst, the term further encompasses physical mixtures of crystalline and amorphous components, as well as intergrowths of at least two different molecular sieve structures, such as, for example, those described in PCT Publication No. WO 98/15496.

In one embodiment, the molecular sieve crystal is an intergrowth material having two or more distinct phases of crystalline structures within one molecular sieve composition. In another embodiment, the molecular sieve crystal comprises at least one intergrown phase of AEI and CHA framework-types. For example, SAPO-18, AlPO-18 and RUW-18 have an AEI framework-type, and SAPO-34 has a CHA framework-type. In a further embodiment, the molecular sieve crystal comprises a mixture of intergrown material and non-intergrown material.

Where the crystalline (catalyst) material of the invention comprises a mixture of CHA and AEI or an intergrowth of a CHA framework and an AEI framework, the material can possess a widely varying AEI/CHA ratio of from about 99:1 to about 1:99, such as from about 98:2 to about 2:98, for example from about 95:5 to about 5:95. In one embodiment, where the material is to be used a catalyst in the conversion of oxygenates to olefins, the intergrowth can preferably be CHA-rich and can advantageously have a AEI/CHA ratio ranging from about 5:95 to about 30:70. In addition, in some cases the intergrown material of the invention may comprise a plurality of intergrown phases with a distribution of different AEI/CHA ratios. The relative amounts of AEI and CHA framework-types in the intergrowth can be determined by a variety of known techniques, including, but not limited to, transmission electron microscopy (TEM) and DIFFaX analysis, using the powder X-ray diffraction pattern of a calcined sample of the catalyst.

In one embodiment, the crystalline molecular sieve can have an average ($d_{50}$) crystal size no greater than 0.15 micron, such as no greater than 0.12, 0.10, 0.07 or 0.05 micron, or such as about 0.01 to about 0.10 micron, about 0.02 to about 0.08 micron, or about 0.02 to about 0.05 micron. Additionally or alternatively, the molecular sieve can be selected so as to have an alpha value between about 100 and about 600, conveniently between about 200 and about 400, or between about 250 and about 350. The alpha value of a molecular sieve is an approximate indication of its catalytic cracking activity compared with a standard silica-alumina catalyst test (with an alpha value of 1). The alpha test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

Without being bound by theory, it is believed that molecular sieves having relatively small crystal sizes, and/or those having relatively large crystal sizes but having too many impurities (e.g., from over-flocculation during isolation and recovery of the molecular sieve during formulation), can be particularly susceptible to having relatively higher zero pass viscosities, when pre-mixed with both the matrix material and the binder component. Therefore, it is believed that the most profound application for the controlled and ordered addition of catalyst composition components is for those molecular sieves that are particularly susceptible to relatively high zero pass viscosities in the absence of said controlled and ordered component addition. Indeed, in many cases, it is further believed that the useful lifetime of a catalyst composition can be particularly impacted by molecular sieve crystal size, by molecular sieve impurity level, by slurry viscosity upon formulation, or by a combination of these three factors.

C. Clay Component

The clay component of the catalyst of this invention can be a natural or synthetic clay. Naturally occurring clays or modified natural occurring clays, e.g., partially dried or dehydrated, milled or micronized, or chemically treated are preferred. Such naturally occurring clays include clays from the kaolinite group, the mica group, the smectite group, and the chlorite group. Examples of kaolinite group clays include kaolinite, dickite and halloysite. Examples of the mica group clays include muscovite, illite, glauconite and biotite. Examples of the smectite group include montmorillonite and vermiculite. Examples of the chlorite group include penninite, clinochlore, ripidolite and chamosite.

Mixed layer clays can also be used. These clays are made of a regular or random stacking of layers composed of members of one or more groups of clay minerals. Chlorite may be seen as a regular alternation of mica and brucite layers. Random mixed layering of three layer clays is common, with examples being mixed layer mica/smectite and chlorite/vermiculite. In regular mixed layer structures such as chlorite, the basal spacing is a combination of that of the individual layers. In random mixed layering there is a non-integral series of reflections from the basal planes. This is shown as a composite reflection intermediate in position between those of the individual layers, or as a spreading of the reflection. Thus, when a significant amount of smectite is interlayered with mica in a random manner, the mica peak will not be sharp, but will be spread toward the lower angle smectite reflection. The amount of spreading depends on the amount of mixed layering that exists.

D. Binder Component

Binders that are used in this invention are materials that act like glue, binding together the molecular sieve crystals and other materials, to form a formulated molecular sieve catalyst composition. Non-limiting examples of binders that can be used in this invention include various types of inorganic oxide sols such as an inorganic oxide sol of alumina or silica, and, in particular, aluminum chlorohydrate, hydrated aluminas, silicas, and/or other inorganic oxide sols.

E. Catalyst Composition Characteristics

One characteristic of the formulated catalyst composition of this invention is that it is highly attrition resistant, as measured by the Attrition Rate Index (ARI) method. The ARI is used over other measurement methods, since many other methods are not sufficient to measure very highly attrition resistant molecular sieve catalysts such as those made according to this invention.

The ARI methodology is similar to the conventional Davison Index method. The smaller the ARI is, the more resistant to attrition the catalyst is. The ARI is measured by adding 6.0±0.1 g of catalyst having a particles size ranging from 53 to 125 microns to a hardened steel attrition jet cup. Approximately 24,000 scc/min of nitrogen gas is bubbled through a water-containing bubbler to humidify the nitrogen. The wet nitrogen passes through an orifice in the jet cup, and exits the attrition apparatus through a porous fiber thimble. Catalyst particles are accelerated in the jet cup, creating collision between the particles and the jet cup, and then are moved into the attrition chamber. Due to the large chamber diameter, catalyst particles can decelerate and fall back to the jet cup below, resulting in particle collision between the falling catalyst particles and particles traveling up from the jet cup. The attrition chamber can thereby act as a disengagement zone such that catalyst particles do not move beyond this zone. The flowing nitrogen carries the finer particles out of the attrition chamber, with the larger particles being retained in the cup. The porous fiber thimble separates the fine catalyst particles from the nitrogen that exits through the thimble. The fine particles remaining in the thimble represent catalyst that has broken apart through attrition.

The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour is weighed. The amount in grams of fine particles divided by the amount of catalyst charged to the attrition cup after the first hour is expressed on per hour basis is the ARI, in wt %/hr.

$$ARI = C/(B+C)/D \times 100\%$$

wherein

B=weight of catalyst left in the cup after the attrition test,

C=weight of collected fine catalyst particles after the first hour of attrition treatment, and D=duration of treatment in hours after the first hour attrition treatment.

In one embodiment, the formulated catalyst composition has an attrition resistance index (ARI) of not greater than 2 wt %/hr, preferably not greater than 1.5 wt %/hr, more preferably not greater than 1 wt %/hr, for example not greater than 0.5 wt %/hr or not more than 0.3 wt %/hr.

The catalyst composition of the invention can also have a relatively high density relative to conventional catalysts. In particular, the catalyst composition of the invention can have a relatively high apparent bulk density (ABD), relative to conventional catalysts.

According to the invention, one way of measuring ABD was using the following procedure. A KIMAX graduated cylinder from KAMLE USA, accurate to 0.05 cc and having a 25 cc capacity, was used to weigh catalyst. The empty cylinder was weighed and the weight recorded as $W_a$. Approximately 25 cc of spray dried and calcined catalyst was poured into the cylinder, and the cylinder was tapped against a lab bench surface at a frequency of 160-170 times per minute for 30 seconds to pack the catalyst inside the cylinder. The weight of the packed cylinder was weighed and recorded as $W_b$. The volume of the catalyst in the cylinder was determined by reading the level of the packed catalyst in the cylinder and recorded as $V_c$. ABD was then calculated as $ABD=(W_b-W_a)/V_c$ in gram per cubic centimeter or g/cc.

In one embodiment, the catalyst composition has an apparent bulk density (ABD) of at least 0.78 g/cc. Preferably, the catalyst composition has an ABD of at least 0.79 g/cc, more preferably at least 0.8 g/cc, and most preferably at least 0.81 g/cc. Generally, the catalyst density is not significantly greater than water. In one embodiment, the catalyst composition has an ABD not greater than 1 g/cc. Preferably, the catalyst composition has an ABD not greater than 0.99 g/cc, and more preferably not greater than 0.98 g/cc.

The catalyst composition of this invention is a dried catalyst composition. It can be dried so that it retains a template within the pore structure of the molecular sieve component, such as by spray drying, or it can be further dried, such as by calcining, which removes the template from the pore structure. Because the dried catalyst is attrition resistant, it is not necessary to calcine the formulated composition prior to use.

For example, the dried composition can be loaded into a reaction system so that conditions within the system remove the template to activate the catalyst for use during operation of the reaction process.

IV. Making Formulated Molecular Sieve Catalyst

A. Components of Formulated Molecular Sieve Catalyst

Molecular sieve catalyst, which contains molecular sieve crystal product, binder and matrix materials, is also referred to as a formulated catalyst. It is made by mixing together molecular sieve crystals (which preferably includes template) and a liquid (preferably water), with matrix material and binder, to form a slurry. The slurry can then be dried (i.e., liquid is removed). Preferably, the slurry can be dried without completely removing the template from the molecular sieve, such as by spray drying. Then, the spray dried catalyst can be calcined to remove additional water and the template material. Once template material is removed, the catalyst is considered activated.

The liquid used to form the slurry can be any liquid conventionally used in formulating molecular sieve catalysts. Non-limiting examples of suitable liquids include water, alcohol, ketones, aldehydes, esters, or a combination thereof. Water is a preferred liquid. The water can come from a variety of sources, including from process water of an oxygenate to olefins reaction process. In the oxygenate to olefins process, a substantial amount of water is produced. With some clean-up, e.g., removal of solids and hydrocarbon contaminants, the water can be re-used in a variety of ways, including making the slurry solution. The water can also be used in the direct manufacture of the molecular sieve itself.

Matrix materials are preferably included in the slurry. Such materials are typically effective in the formulated molecular sieve catalyst product as thermal sinks assisting in shielding heat from the catalyst composition, for example, during regeneration. They can further act to density the catalyst composition, increase catalyst strength such as crush strength and attrition resistance, and to control the rate of conversion in a particular process. Non-limiting examples of matrix materials include one or more of: rare earth oxides, metal oxides including titania, zirconia, magnesia, thoria, beryllia, quartz, silica or sols, and mixtures thereof, for example, silica-magnesia, silica-zirconia, silica-titania, silica-alumina, and silica-alumina-thoria.

One preferred type of matrix material used to make the catalyst of this invention is clay. Particularly preferred clays include kaolins such as, for example, Dixie, McNamee, Georgia, and Florida clays. Optionally, the matrix material, preferably any of the clays, can be calcined, acid treated, and/or chemically treated before being used as a slurry component.

In a particular embodiment, the clay can have a low iron or titania content, and is most preferably kaolin clay. Kaolin has been found to form a pumpable, high solid content slurry; it typically has a low fresh surface area, and can pack together easily due to its platelet structure.

Preferably, the clay can have an average particle size of from about 0.05 μm to about 0.75 μm; more preferably from about 0.1 μm to about 0.6 μm. It is also desirable that the clay material have a particle size distribution such that $d_{90}$ can be less than about 1.5 μm, preferably less than about 1 μm.

Binders are also included in the slurry used to make the formulated molecular sieve catalyst of this invention. In one embodiment of the invention, the binder is an alumina-containing sol, preferably aluminium chlorohydrate. Upon calcining, the inorganic oxide sol, is converted into an inorganic oxide binder component, which is particularly effective in forming an attrition resistant molecular sieve catalyst composition. For example, an alumina sol will typically convert to an aluminium oxide binder following heat treatment.

Aluminium chlorohydrate, a hydroxylated aluminium based sol containing a chloride counter ion, also known as aluminium chlorohydrol, has the general formula

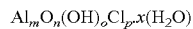

$$Al_mO_n(OH)_oCl_p\cdot x(H_2O)$$

wherein m is 1 to 20, n is 1 to 8, o is 5 to 40, p is 2 to 15, and x is 0 to 30. In one embodiment, the binder is $Al_{13}O_4(OH)_{24}Cl_7\cdot 12(H_2O)$ as is described in G. M. Wolterman, et al., *Stud. Surf. Sci. and Catal.*, Vol. 76, pp. 105-144, Elsevier, Amsterdam, 1993, which is herein incorporated by reference. In another embodiment, one or more binders are present in combination with one or more other non-limiting examples of alumina materials such as aluminium oxyhydroxide, γ-alumina, boehmite and transitional aluminas such as β-alumina, γ-alumina, δ-alumina, ε-alumina, κ-alumina, and ρ-alumina, aluminium trihydroxide, such as gibbsite, bayerite, nordstrandite, doyelite, and mixtures thereof.

Aluminum chlorohydrate can be prepared by dissolving either metallic aluminum or hydrated alumina in hydrochloric acid under controlled conditions, and is available commercially in different forms, such as solid products; for example, the solid of chemical formula $Al_2(OH)_5Cl\cdot n(H_2O)$ or as preprepared, commercially available, aqueous solutions. Other non-limiting examples of useful aluminum oxide precursors that may be used according to this invention include aluminum hexahydrate, aluminum pentachlorohydrate ($Al_2(OH)Cl_5$), aluminum tetrachlorohydrate ($Al_2(OH)_2Cl_4$), aluminum trichlorohydrate ($Al_2(OH)_3Cl_3$), aluminum dichlorohydrate ($Al_2(OH)_4Cl_2$), aluminum sesquichlorohydrate ($Al_2(OH)_{4.5}Cl_{1.5}$).

Other non-limiting examples of binders useful according to this invention include precursors of aluminum-zirconium oxides. Such precursors include, but are not limited to, aluminum zirconium chlorohydrates; for example, aluminum zirconium trichlorohydrate, aluminum zirconium tetrachlorohydrate, aluminum zirconium pentachlorohydrate, aluminum zirconium octachlorohydrate, aluminum zirconium chlorhydrex, aluminum zirconium chlorhydrex glycine complexes (e.g., aluminum zirconium trichlorohydrex glycine complex, aluminum zirconium tetrachlorohydrex glycine complex, aluminum zirconium pentachlorohydrex glycine complex, and aluminum zirconium octachlorohydrex glycine complex). In the absence of glycine, these materials form gels in aqueous solutions. Reheis Chemicals Inc., Berkeley Heights, N.J. produces a variety of aluminum zirconium chlorohydrates. These materials can be prepared from a variety of zirconium starting materials such as zirconyl chloride ($ZrOCl_2$), zirconyl hydroxychloride ($ZrO(OH)Cl$), zirconium hydroxy carbonate paste ($ZrO(OH)(CO_3)_{0.5}$), and combinations of these zirconium starting materials, with a hydrated aluminum solution, such as a solution of aluminum chlorohydrate, aluminum hexahydrate, aluminum sesquichlorohydrate or aluminum dichlorohydrate solution, or a solution obtained by combining one or several of these aluminum species solutions.

In another embodiment, the binders are alumina sols, predominantly comprising aluminium oxide, optionally, including silicon. In yet another embodiment, the binders are peptised alumina made by treating alumina hydrates such as pseudobohemite, with an acid, preferably a non-halogen acid, to prepare sols or aluminium ion solutions. Non-limiting examples of commercially available colloidal alumina sols include Nalco 8676 available from Nalco Chemical Co., of Napierville, Ill., and AL20DW available from Nyacol Nano Technology Inc., of Boston, Mass.

In a preferred embodiment, the amount of binder used to prepare the molecular sieve catalyst composition is at least 5 wt %, based on total weight of the material used to make the composition, excluding liquid (i.e., after drying), particularly excluding water. Preferably the amount of binder used to prepare the molecular sieve catalyst is at least 8 wt %, and more preferably at least 10 wt %, based on total weight of the material used in making the catalyst, excluding liquid (i.e., after drying). It is also preferred that the amount of binder used to prepare the molecular sieve catalyst is not greater than about 50 wt %, preferably not greater than 40 wt %, and more preferably not greater than 30 wt %, based on total weight of the material used in making the catalyst, excluding liquid (i.e., after drying).

B. Making a Slurry with Molecular Sieve Crystals

The molecular sieve crystals are mixed with clay and binder, as well as liquid solvent component, to form a slurry. The components can be mixed in any order. However, in a particularly preferred embodiment, a molecular sieve is first added to a combination of binder and liquid, followed by the addition of matrix (preferably clay) to that binder-sieve mixture to form a binder-sieve-matrix mixture. The binder-sieve-matrix mixture can advantageously be thoroughly stirred, preferably using a rotor-stator mixing unit and/or a milling apparatus each having appropriate characteristics. Examples of desired characteristics are detailed above.

The molecular sieve crystals, clay, and binder are mixed together to form a slurry having a desired solids content. The solids content should be sufficiently high, otherwise a less attrition resistant catalyst will be formed.

In one embodiment, molecular sieve crystals, clay, and binder are mixed together to form a slurry having a solids content of at least 40 wt %, based on total weight of the slurry mixture. Preferably, molecular sieve crystals, clay, binder and water are mixed to form a slurry having a solids content of at least 41 wt %, more preferably at least 43 wt %, and most preferably at least 44 wt %, based on the total weight of the slurry. In some embodiments, molecular sieve crystals, clay, binder and water are mixed to form a slurry having a solids content of not greater than 75%, for example not greater than 70%, not greater than 65%, not greater than 60%, not greater than 55%, or not greater than 50%, based on the total weight of the slurry.

The solids content can be measured using any conventional means. However, a CEM MAS 700 microwave muffle furnace (CEM Corp., Matthews, N.C.) is particularly preferred to give results consistent with the values recited herein. It is also preferred that the slurry have a solids content of not greater than 60 wt %, based on total weight of the slurry. Preferably, the slurry has a solids content of not greater than 58 wt %, more preferably not greater than 56 wt %, most preferably not greater than 54 wt %, based on total weight of the slurry.

In another embodiment of the invention, the molecular sieve crystals, clay, and binder are mixed together to form a slurry mixture at a binder to molecular sieve weight ratio of at least 0.20:1. Preferably, the molecular sieve crystals, clay, and binder are mixed together at a binder to molecular sieve weight ratio of at least 0.22:1, more preferably at least 0.24:1, and most preferably at least 0.25:1. It is also preferred that the crystals, clay, and binder be mixed together at a binder to molecular sieve weight ratio of not greater than 0.8:1, preferably not greater than 0.6:1.

In another embodiment, the molecular sieve crystals, clay, and binder are mixed together to form a slurry mixture at a binder content of at least 5 wt %, preferably at least 8 wt %, and more preferably at least 10 wt %, based on total weight of the mixture, excluding liquid (e.g., water). It is also preferred in an embodiment that the molecular sieve crystals, clay, and binder are mixed together to form a slurry mixture at a binder content of not greater than 35 wt %, preferably not greater than 30 wt %, for example not greater than 25 wt %, based on total weight of the mixture, excluding liquid (e.g., water).

The temperature at which the slurry is made can range. Examples of such conditions include temperatures ranging from 0° C. to 100° C., preferably from 10° C. to 90° C., more preferably from 15° C. to 80° C., for example from 20° C. to 70° C.

In-tank or batch operation can be operated for some duration to ensure proper mixing and viscosity. In one embodiment, the rotor-stator mixer is in-tank operated for a period of at least 1 hours, preferably at least 1.5 hours, more preferably at least 2 hours, and most preferably at least 2.5 hours. In a preferred embodiment, mixing of slurry components is performed for not more than 150 hours, preferably not more than 120 hours, most preferably not more than 100 hours. Other preferred batch mixing conditions include mixing at a temperature from 30° C. to 50° C. for a period of from 1 hours to 80 hours, preferably from 1.5 hours to 75 hours, more preferably from 2 hours to 50 hours, most preferably from 2.5 hours to 36 hours.

C. Drying the Slurry

In one embodiment, the slurry of the molecular sieve, binder, and matrix materials is fed to a forming unit that produces a dried molecular sieve catalyst composition. Non-limiting examples of forming units include spray dryers, pelletizers, extruders, etc. In a preferred embodiment, the forming unit is spray dryer. Typically, the forming unit is maintained at a temperature sufficient to remove most of the liquid (e.g., water) from the slurry.

When a spray dryer is used as the forming (or drying) unit, typically, the slurry of the molecular sieve, matrix material and binder, is co-fed to the drying unit with a drying gas. In one embodiment the drying unit has an average inlet temperature ranging from 150° C. to 550° C., and an average outlet temperature ranging from 50° C. to about 400° C.

In one embodiment, the slurry is passed through a nozzle distributing the slurry into small droplets, resembling an aerosol spray, into a drying chamber. Atomization is achieved by forcing the slurry through a single nozzle or multiple nozzles with a pressure drop in the range from about 100 psia to about 1000 psia (about 690 kPaa to about 6900 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a partially, substantially or totally dried molecular sieve catalyst composition.

In another embodiment of the invention, the slurry is dried in a drying unit and then calcined. In one embodiment, the slurry is dried to form a dried molecular sieve catalyst composition, and the dried catalyst composition is calcined. In general, calcination further hardens and/or activates the dried molecular sieve catalyst composition. An acceptable calcination environment is air that typically includes a small amount of water vapour. Typical calcination temperatures are in the range from about 400° C. to about 1000° C., preferably from about 450° C. to about 800° C., and most preferably from about 470° C. to about 700° C., preferably in a calcination environment such as air, nitrogen, helium, flue gas (combustion product lean in oxygen), steam, or any combination thereof.

The dried or formulated molecular sieve catalyst composition can be calcined in many types of devices, including but not limited to, rotary calciners, fluid bed calciners, batch ovens, and the like. Calcination time is typically dependent on the degree of hardening of the molecular sieve catalyst composition and the temperature.

In a preferred embodiment, the molecular sieve catalyst composition is heated in nitrogen-containing gases such as air, or mixtures of nitrogen-containing gases and other gases (such as water vapor) at a temperature from about 450° C. to about 700° C. Heating can be carried out for a period of time typically from 1 minute to 15 hours, preferably from 2 minutes to about 10 hours, more preferably from about 3 minutes to about 5 hours, and most preferably from about 5 minutes to about 4 hours.

V. Methods of Using Catalyst

The molecular sieve catalyst product made according to this invention is useful in a variety of processes including cracking of, for example, a naphtha feed to light olefin(s) (U.S. Pat. No. 6,300,537) or higher molecular weight (MW) hydrocarbons to lower MW hydrocarbons; hydrocracking of, for example, heavy petroleum and/or cyclic feedstock; isomerization of, for example, aromatics such as xylene; polymerization of, for example, one or more olefin(s) to produce a polymer product; reforming; hydrogenation; dehydrogenation; dewaxing of, for example, hydrocarbons to remove straight chain paraffins; absorption of, for example, alkyl aromatic compounds for separating out isomers thereof; alkylation of, for example, aromatic hydrocarbons such as benzene and alkyl benzene, optionally with propylene to produce cumene or with long chain olefins; transalkylation of, for example, a combination of aromatic and polyalkylaromatic hydrocarbons; dealkylation; hydrodecyclization; disproportionation of, for example, toluene to make benzene and paraxylene; oligomerization of, for example, straight and branched chain olefin(s); and dehydrocyclization.

Preferred processes include processes for converting naphtha to highly aromatic mixtures; converting light olefin(s) to gasoline, distillates and lubricants; converting oxygenates to olefin(s); converting light paraffins to olefins and/or aromatics; and converting unsaturated hydrocarbons (ethylene and/or acetylene) to aldehydes for conversion into alcohols, acids, and esters.

The most preferred process of the invention is a process directed to the conversion of a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms. Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

The catalyst made according to the process of this invention has an attrition resistance that is suitable for use in a wide variety of reaction processes. Examples of such processes include a fixed-bed process, or more typically as a fluidized-bed process (including a turbulent-bed process), such as a continuous fluidized-bed process, and particularly a continuous high-velocity, fluidized-bed process.

VI. Other Preferred Embodiments

Additionally or alternatively, the invention can include the following embodiments.

Embodiment 1. A method of making a molecular sieve catalyst composition comprising the steps of:
  a) combining molecular sieve crystals with binder and liquid to form a binder-sieve mixture;
  b) combining the binder-sieve mixture with matrix material to form a binder-sieve-matrix mixture;
  c) mixing the binder-sieve-matrix mixture under conditions sufficient to form a slurry having a solids content of at least 40 wt %, based on total weight of the slurry;
  d) progressing the mixing until slurry viscosity decreases without significant additional dilution of the slurry, so that the slurry solids content does not significantly decrease; and
  e) drying the decreased viscosity slurry to produce a dried molecular sieve catalyst composition having an attrition rate index of not greater than 2.0 wt %/hr,
  wherein the combining in step b) and the mixing in step c) result in a maximum viscosity below 30,000 cPs, wherein the decreased viscosity slurry formed in step d) has a final viscosity not greater than 15,000 cPs, and wherein the ratio of the final viscosity to the maximum viscosity is from 20% to 65%.

Embodiment 2. The method of embodiment 1, wherein the slurry has a solids content between 40 wt % and 60 wt %, preferably between 40 wt % and 50 wt %, based on total weight of the slurry.

Embodiment 3. The method of embodiment 1 or embodiment 2, wherein progressing of the mixing in step d) occurs with no additional dilution of the slurry, so that the slurry solids content does not decrease.

Embodiment 4. The method of any of the previous embodiments, wherein the dried molecular sieve catalyst composition has an attrition rate index of not greater than 1.0 wt %/hr, alternately not greater than 0.5 wt %/hr or not greater than 0.3 wt %/hr.

Embodiment 5. The method of any of the previous embodiments, wherein the combining in step b) and the mixing in step c) result in a maximum viscosity below 25,000 cPs.

Embodiment 6. The method of any of the previous embodiments, wherein the decreased viscosity slurry formed in step d) has a final viscosity not greater than 14,000 cPs, alternately not greater than 13,000 cPs.

Embodiment 7. The method of any of the previous embodiments, wherein the ratio of the maximum viscosity to the final viscosity is from 30% to 55%, preferably from 35% to 50%.

Embodiment 8. The method of any of the previous embodiments, wherein the slurry is dried in step e) by a combination of spray drying and calcining.

Embodiment 9. The method of any of the previous embodiments, wherein the matrix material is a natural or synthetic clay, preferably kaolin clay.

Embodiment 10. The method of any of the previous embodiments, wherein the binder comprises an inorganic oxide sol of alumina, preferably an aluminum-containing chlorohydrate.

Embodiment 11. The method of any of the previous embodiments, wherein the molecular sieve particles are aluminosilicate molecular sieve crystals, metalloaluminophosphate molecular sieve crystals, or a mixture or intergrowth thereof.

Embodiment 12. The method of embodiment 11, wherein the metalloaluminophosphate molecular sieve crystals are selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal-containing versions thereof, mixtures thereof, and intergrowths thereof.

Embodiment 13. The method of embodiment 11, wherein the molecular sieve particles are aluminosilicate molecular sieve crystals having a silicon-to-aluminum ratio of at least 10, preferably at least 20, for example at least 30, at least 40, at least 50, at least 75, or at least 100.

Embodiment 14. A process for making an olefin product from an oxygenate feedstock comprising the steps of:

a) making a dried molecular sieve catalyst composition according to the method of any of the previous embodiments; and b) contacting the dried metalloaluminophosphate molecular sieve catalyst with the oxygenate feedstock under conditions sufficient to form the olefin product comprising ethylene and propylene, wherein the selectivity of the dried metalloalumino-phosphate molecular sieve catalyst for the combination of ethylene and propylene is at least 70%, preferably at least 72%, for example at least 73%, at least 74%, at least 75%, at least 78%, or at least 80%, based on the total weight of carbonaceous material contacting the catalyst.

Embodiment 15. A process for making a (co)polymer product comprising the steps of:

a) making an olefin product comprising ethylene and propylene from an oxygenate feedstock according to the method of embodiment 14; and b) contacting at least one of the ethylene and propylene from the olefin product, and optionally one or more other polymerizable monomers, with a polymerization catalyst under conditions sufficient to form the (co)polymer product, wherein the (co)polymer product comprises a combined ratio of ethylene and/or propylene repeat units to other polymerizable monomer repeat units that is more than 50 wt %, preferably more than 70 wt %, for example more than 75 wt %, more than 80 wt %, more than 85 wt %, more than 90 wt %, more than 95 wt %, or more than 99 wt %.

VII. Examples of Methods of Making Relatively Low Max. Viscosity Slurry

Comparative Example 1

A 1.8 kg slurry was made by (1) adding 452.8 g of aluminum chlorohydrate solution (LOI: 75.25%) from Reheis Chemical Inc., Berkeley Heights, N.J., to 216.6 g of de-ionized water and mixed using a Yamato LR400D™ homogenizer from Yamato Scientific Americas, Orangeburg, N.Y., at about 500 rpm for about 5 minutes; (2) adding 727.5 g of EMM-2 sieve (LOI: 49.9%) and mixed using a Silverson high-shear mixer (Silverson Machines Inc., East Longmeadow, Mass.) at about 6000 rpm for about 3 minutes; and (3) adding 403.1 g of kaolin clay (LOI: 16.61%) from Engelhard Corporation, Iselin, N.J., while mixing using a Yamato homogenizer at about 700 rpm for about 10 minutes. This slurry was sent to an in-line high-shear mixer from Silverson Machines Inc. The milling was conducted using a Silverson L4RT-W™ high-shear mixer with a slot screen (Silverson Machines Inc., East Longmeadow, Mass.) at about 7500 rpm. The slurry was fed to the in-line mixer inlet by a Moyno metering feed pump from Moyno Inc., Springfield, Ohio, at about 1000 cc/min., and the milled material was recycled back to the funnel connected to the inlet of the Moyno pump.

"Milled for one pass" is defined as the entire slurry content having gone through the mill once, based on calculation, for example, at about 1000 cc/min feed rate; for a 1000-cc slurry, "milled for one minute" would thus be the same as "milled for one pass." A "zero pass" milled material represents a slurry that is mixed but has not yet gone through a mill yet.

Viscosity values of the slurry of Comparative Example 1 milled for various passes is presented in Table 1 below.

TABLE 1

| Viscosity of a pre-mixed slurry (Comp. Ex. 1) after milling Pre-mixing | |
|---|---|
| Milling (passes) | Viscosity (cPs) @ 10 rpm |
| 0 | 33200 |
| 30 | 15700 |
| 60 | 14000 |
| 90 | 12400 |
| 120 | 12300 |

The slurry, after being milled for about 120 passes, had a solids content of about 44.4%, a pH of about 3.6 measured at 23° C., and a density of about 1.44 g/cc. It was spray dried using a Yamato DL-41™ spray dryer with a two-fluid atomizer from Yamato Scientific Americas, Orangeburg, N.Y., at an inlet temperature of about 350° C. and at a feed rate of about 44 g/min. The spray dried product was calcined at about 650° C. for about 2 hours, i.e., about one hour in nitrogen at a flow of about 2000 cc/min and about one hour in air at a flow of about 2000 cc/min. The calcined material was screened to give a fraction of about 53 to about 120 microns in size to be used for the attrition measurement, using a jet cup attrition unit. The attrition loss rate was determined to be about 0.33 wt %/hr.

Example 2

A 1.8 kg slurry was made by (1) adding 452.8 g of aluminum chlorohydrate solution (LOI: 75.25%) from Reheis Chemical Inc., Berkeley Heights, N.J., to 216.8 g of de-ionized water and mixed using a Yamato LR400D™ homogenizer from Yamato Scientific Americas, Orangeburg, N.Y., at about 500 rpm for about 5 minutes; and (2) adding 727.5 g of EMM-2 sieve (LOI: 49.9%) and mixed using a Silverson high-shear mixer (Silverson Machines Inc., East Longmeadow, Mass.) at about 6000 rpm for about 3 minutes. This slurry was transferred to an in-line high-shear mixer from Silverson Machines Inc. The milling was conducted using a Silverson L4RT-W™ high-shear mixer with a slot screen (Silverson Machines Inc., East Longmeadow, Mass.) at about 7500 rpm. The slurry was fed to the in-line mixer inlet by a Moyno metering feed pump from Moyno Inc., Springfield, Ohio, at about 1000 cc/min., and the milled material was recycled back to the funnel connected to the inlet of the Moyno pump. During milling, (3) 403.1 g of kaolin clay (LOI: 16.61%) from Engelhard Corporation, Iselin, N.J., was added. The slurry was milled for a variety of number of passes, the viscosity values of which are given in Table 2 below.

TABLE 2

Viscosity of a slurry made by controlled addition (Ex. 2)
Controlled Addition

| Milling (passes) | Viscosity (cPs) @ 10 rpm |
|---|---|
| 0 | 23400 |
| 30 | 14500 |
| 90 | 12600 |
| 120 | 12000 |

The slurry, after being milled for about 120 passes, had a solids content of about 44.6%, a pH of about 3.8 measured at 23° C., and a density of about 1.45 g/cc. It was spray dried using a Yamato DL-41™ spray dryer with a two-fluid nozzle atomizer from Yamato Scientific Americas, Orangeburg, N.Y., at an inlet temperature of about 350° C. and at a feed rate of about 44 g/min. The spray dried product was calcined at about 650° C. for about 2 hours, i.e., about one hour in nitrogen at a flow of about 2000 cc/min and about one hour in air at a flow of about 2000 cc/min. The calcined material was screened to give a fraction of about 53 to about 120 microns in size to be used for the attrition measurement, using a jet cup attrition unit. The attrition loss rate was determined to be about 0.37 wt %/hr.

From Tables 1 and 2, it can be seen that the slurry made by mixing the EMM-2 sieve with the ACH binder and adding kaolin clay during milling (Example 2) has a substantially lower zero pass viscosity than the one that is prepared by pre-mixing all three components (Example 1).

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed is:

1. A method of making a molecular sieve catalyst composition comprising the steps of:
   a) combining molecular sieve crystals with binder and liquid to form a binder-sieve mixture;
   b) combining the binder-sieve mixture with matrix material to form a binder-sieve-matrix mixture;
   c) mixing the binder-sieve-matrix mixture under conditions sufficient to form a slurry having a solids content of at least 40 wt %, based on total weight of the slurry;
   d) progressing the mixing until slurry viscosity decreases without significant additional dilution of the slurry, so that the slurry solids content does not significantly decrease; and
   e) drying the decreased viscosity slurry to produce a dried molecular sieve catalyst composition having an attrition rate index of not greater than 2.0 wt %/hr,
   wherein the combining in step b) and the mixing in step c) result in a maximum viscosity below 30,000 cPs, wherein the decreased viscosity slurry formed in step d) has a final viscosity not greater than 15,000 cPs, and wherein the ratio of the final viscosity to the maximum viscosity is from 20% to 65%.

2. The method of claim 1, wherein the slurry has a solids content between 40 wt % and 50 wt %, based on total weight of the slurry.

3. The method of claim 1, wherein progressing of the mixing in step d) occurs with no additional dilution of the slurry, so that the slurry solids content does not decrease.

4. The method of claim 1, wherein the dried molecular sieve catalyst composition has an attrition rate index of not greater than 1.0 wt %/hr.

5. The method of claim 1, wherein the dried molecular sieve catalyst composition has an attrition rate index of not greater than 0.5 wt %/hr.

6. The method of claim 1, wherein the combining in step b) and the mixing in step c) result in a maximum viscosity below 25,000 cPs.

7. The method of claim 1, wherein the decreased viscosity slurry formed in step d) has a final viscosity not greater than 14,000 cPs.

8. The method of claim 1, wherein the decreased viscosity slurry formed in step d) has a final viscosity not greater than 13,000 cPs.

9. The method of claim 1, wherein the ratio of the final viscosity to the maximum viscosity is from 30% to 55%.

10. The method of claim 1, wherein the ratio of the final viscosity to the maximum viscosity is from 35% to 50%.

11. The method of claim 1, wherein the slurry is dried in step e) by a combination of spray drying and calcining.

12. The method of claim 1, wherein the matrix material is a natural or synthetic clay.

13. The method of claim 1, wherein the matrix material is a kaolin clay.

14. The method of claim 1, wherein the binder comprises an inorganic oxide sol of alumina.

15. The method of claim 1, wherein the binder comprises an aluminum-containing chlorohydrate.

16. The method of claim 1, wherein the molecular sieve particles are aluminosilicate molecular sieve crystals, metalloaluminophosphate molecular sieve crystals, or a mixture or intergrowth thereof.

17. The method of claim 1, wherein the molecular sieve particles are metalloaluminophosphate molecular sieve crystals selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal-containing versions thereof, mixtures thereof, and intergrowths thereof.

18. The method of claim 1, wherein the molecular sieve particles are aluminosilicate molecular sieve crystals having a silicon-to-aluminum ratio of at least 10.

19. The method of claim 1, wherein the molecular sieve particles are aluminosilicate molecular sieve crystals having a silicon-to-aluminum ratio of at least 50.

20. The method of claim 1, wherein the combining of the molecular sieve crystals, the binder, and the matrix material in a single step results in a maximum viscosity of 30,000 cPs or higher upon mixing.

* * * * *